United States Patent [19]

Pepe et al.

[11] Patent Number: 5,354,880
[45] Date of Patent: Oct. 11, 1994

[54] CYCLIC SILYLUREAS AND PROCESS OF PREPARATION

[75] Inventors: Enrico J. Pepe, Amawalk, N.Y.; Curtis L. Schilling, Jr., Marietta, Ohio; Everett W. Bennett, Easthampton, Mass.

[73] Assignee: OSi Specialties, Inc., Danbury, Conn.

[21] Appl. No.: 993,304

[22] Filed: Dec. 18, 1992

[51] Int. Cl.$^5$ ................................................ C07F 7/10
[52] U.S. Cl. .................................... 556/407; 556/413; 556/415; 523/176; 524/425
[58] Field of Search ........................ 556/407, 413, 415; 523/176; 524/425

[56] References Cited

U.S. PATENT DOCUMENTS

| | | | |
|---|---|---|---|
| 3,146,250 | 8/1964 | Speier | 260/448.2 |
| 3,170,941 | 2/1965 | Speier | 260/448.2 |
| 3,179,622 | 4/1965 | Haluska | 556/407 X |
| 3,361,783 | 1/1968 | Fink | 556/407 X |
| 3,632,557 | 1/1972 | Brode et al. | 260/77.5 TB |
| 3,725,449 | 4/1973 | Golitz et al. | 556/407 |
| 3,793,253 | 2/1974 | Quiring et al. | 556/407 X |
| 4,143,060 | 3/1979 | Wagner et al. | 556/407 |
| 4,374,237 | 2/1983 | Berger et al. | 528/28 |
| 4,578,492 | 3/1986 | Pratt et al. | 556/407 |
| 4,725,659 | 2/1988 | Pohl et al. | 528/17 |
| 4,801,673 | 1/1989 | Bosch et al. | 528/34 |
| 4,804,771 | 2/1989 | Pepe | 556/407 |
| 4,849,263 | 7/1989 | Pepe et al. | 427/336 |
| 5,017,717 | 5/1991 | Wright et al. | 556/413 |
| 5,030,746 | 7/1991 | Schilling | 556/413 X |
| 5,082,962 | 1/1992 | Schilling | 556/413 X |
| 5,110,974 | 5/1992 | King et al. | 556/407 |
| 5,117,024 | 5/1992 | Dinh et al. | 556/413 |

OTHER PUBLICATIONS

Speier, John L., C. A. Roth, and John W. Ryan, "Syntheses of (3-Aminoalkyl)silicon Compounds", *J. Org. Chem.*, vol. 36, No. 21, 1971, pp. 3121–3126.

Baceiredo, Antoine, Guy Bertrand, Pierre Mazerolles and Jean Pierre Majoral, "Curtius Rearrangement in the Silicon Series: Mechanisms and Synthetic Applications", *Chemical Abstracts* 101:7252w, vol. 101, 1984, p. 7250.

*Primary Examiner*—Paul F. Shaver
*Attorney, Agent, or Firm*—St. Onge Steward Johnston & Reens

[57] ABSTRACT

This invention provides a class of cyclic silylureas and a process of preparing them, which process comprises reacting a cyclosilazane with an isocyanate containing moiety; a class of cyclosilazanes and process for making them, which process comprises heating an aminoalkylalkoxysilane in the presence of a basic catalyst at a temperature less than 100° C. at subatmospheric pressure; and aminoalkylalkoxysilanes and a process for making them, which process comprises reacting a nitrile and a vinylsilane while heating in the presence of a base selected from the group consisting (a) an alkali metal, (b) alkali metal alkoxide, (c) an alkali metal amide, (d) an alkali metal hydride and (e) mixtures thereof to form a reaction product which is subsequently hydrogenated.

19 Claims, No Drawings

CYCLIC SILYLUREAS AND PROCESS OF PREPARATION

BACKGROUND OF THE INVENTION

1. Field of the Invention

The present invention relates to cyclic silylureas and their preparation, to their cyclosilazane starting materials and their preparation, and to aminoalkylalkoxysilanes used to make cyclosilazanes and their preparation. More particularly, the present invention relates to cyclic silylureas which retain the cyclosilazane ring structure after formation. Cyclic silylureas of the present invention are used as additives in formulations for room temperature vulcanizing (RTV) coatings, adhesives and sealants to impart fast cure and reduced volatile organic compound (VOC) release, such as the release of methanol.

2. Prior Art

There has been a continuing need in the adhesives and sealant industry for faster-curing silicone systems, allowing more rapid assembly of full-strength articles of manufacture, including automobiles. There has been a more recent need to have such systems cure with lower, more environmentally acceptable levels of volatile organic compounds.

Fast curing can be attained with systems based on a polyfunctional silazane (i.e., compounds with Si—N bonds) as curing agents. Such systems typically cure by releasing low molecular weight organic amines or ammonia, which are environmentally undesirable because of unacceptable odor and toxicity. Cyclosilazanes and derivatives are compounds with Si—N bonds which cure at high rates by cleaving the Si—N bond without release of volatile organic compounds.

Cyclosilazanes have not achieved commercial acceptance in the industry because of the inability to produce them easily and in large quantity. Earlier attempts at making even small quantities have suffered from a combination of low efficiency and high cost, coupled in some cases with generation of high levels of hazardous waste by-products which require costly disposal by incineration or land-filling.

Thus, there is a need for cyclosilazane-based curing agents for silicone and related adhesive systems which can be prepared in commercial equipment with high efficiency at practical cost of production and waste disposal, and which provide high curing rates with reduced generation of volatile organic compounds. Surprisingly, that need is met by the cyclic silylureas and cyclosilazanes of the present invention.

SUMMARY OF THE INVENTION

In accordance with the present invention there is provided a class of cyclic silylureas and a process of preparing them by contacting a cyclosilazane with an isocyanate containing moiety. In forming the cyclic silylureas of the present invention, the cyclosilazane ring structure is retained. The resultant cyclic silylurea is stable on storage, but is highly reactive to moisture, especially when exposed to ambient moisture in air.

Another embodiment of the present invention provides a class of cyclosilazanes and a process for making them. The cyclosilazanes of the present invention have an Si—N bond, four carbon atoms in the ring, hydrogen as the exocyclic substituent on the nitrogen atom, and exocyclic substituents on the silicon which do not interfere sterically during cyclic silylurea formation. Optionally, the cyclosilazane can have exocyclic alkyl groups on a ring carbon atom. The process of making the cyclosilazanes of the present invention is rapid, easy to perform, and produces the desired cyclosilazane in high yield under mild conditions.

In another embodiment of the present invention there are provided aminoalkylalkoxysilanes and their preparation. These aminoalkylalkoxysilanes are used to make cyclosilazanes. The process for making the aminoalkylalkoxysilane produces a silicon compound having a sterically hindered nitrile group, which process is easy, rapid, and results a high yield of product.

Still another embodiment of the present invention provides a sealant formulation containing the cyclic silylurea which cures or sets up rapidly.

DETAILED DESCRIPTION OF THE INVENTION

Cyclic silylureas of the present invention are prepared by a process which comprises contacting a cyclosilazane with an isocyanate group containing moiety according to Process A as follows:

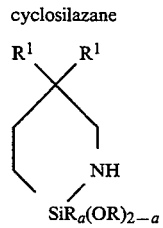
cyclosilazane

Formula I

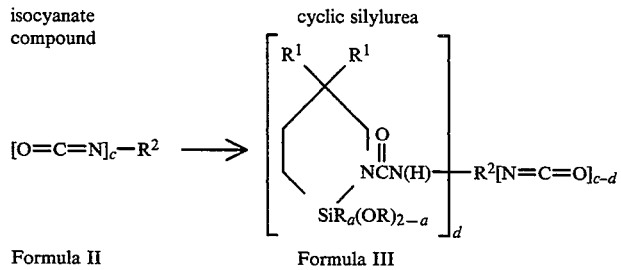
isocyanate compound

Formula II cyclic silylurea

Formula III

In Formula I (cyclosilazane) and Formula III (cyclic silylurea), R is an alkyl group having 1 to 3 carbon atoms, and preferably each R is a methyl group or an ethyl group. $R^1$ in Formulae I and III and is selected from the group consisting of (i) hydrogen, (ii) a linear or branched alkyl group having 1 to 6 carbon atoms, and (iii) an aryl group having 6 to 8 carbon atoms. Preferably, each $R^1$ in Formulae I and III is a hydrogen or a methyl group. In Formulae I and III, a is 0, 1 or 2. It is to be understood that the R groups shown in Formulae I and III can be the same as or different from one another; likewise, the $R^1$ groups can be the same as or different from one another.

In Formulae II and III, c is a number ranging from 1 to 5 inclusive, preferably 1 to 3, and d is a number less than or equal to c. It is understood that when c has a value of 2 or more, not all of the isocyanate groups need to be reacted with the cyclosilazane. Accordingly, there can be unreacted isocyanates in the final cyclic silylurea.

Any isocyanate containing moiety ($R^2[N=C=O]_c$) having at least one isocyanate group capable of reacting with a cyclosilazane can be employed in the process of the present invention. $R^2$ can be a mono-, di- or polyvalent organic or organosilicone monomer or polymer. In Formulae II and III, $R^2$ is selected from the group consisting of (i) through (vi) below.

(i) A alkyl group having 1 to 11 carbon atoms, preferably 1 to 5 carbon atoms, and most preferably 1 or 4 carbon atoms. Suitable alkyl groups can include, for example, methyl, ethyl, propyl, isopropyl and butyl.

(ii) A aryl group having 6 to 16 carbon atoms, preferably 6 to 10 carbon atoms, and most preferably 6 carbon atoms. Suitable aryl groups can include, for example, phenyl and naphthyl.

(iii) An alkaryl or aralkyl group having 7 to 20 carbon atoms, preferably 7 to 11 carbon atoms, and most preferably 7 carbon atoms. Suitable alkaryl and aralkyl groups can include, for example, benzyl, tolyl, xylylpropyl, phenylethyl, and 3-isopropenyl-dimethylbenzyl.

(iv) An alkarylene group having 7 to 28 carbon atoms, preferably 7 to 17 carbon atoms, and most preferably 7 or 13 carbon atoms. Suitable alkarylene groups can include, for example, 2,4-tolylene as in toluene diisocyanate (TDI), xylylene, bis(phenylene)methane as in methylene bis-phenylene diisocyanate (MDI), and other such divalent alkyl-substituted arylene groups.

(v) An alkylene group having 2 to 18 carbon atoms, preferably 6 to 13 carbon atoms, and most preferably 6, 10, or 13 carbon atoms. Suitable alkylene groups can include, for example, hexamethylene as in hexamethylene diisocyanate, isophoronylene as in isophorone diisocyanate, and bis(cyclohexylene)methane, and other such divalent alkylene groups.

(vi) A polymeric moiety. As used herein, "polymeric moiety" can include oligomeric compounds. These moieties are typically employed in RTV coatings, adhesives, and sealant, electrical applications, and urethane foams. Such moieties can include, for example, a polyester, a polyether, a polydiene, a polyurethane, a poly(meth)acrylate, and a polyorganosilicone. Such moieties, when combined with the isocyanate functionality, are commercially available as polymeric isocyanates and are well known in the art, including Desmodur ™ N, a partial hydrolysis product of hexamethylene diisocyanate.

While (i) through (v) above list $R^2$ groups which are hydrocarbon groups, it is understood that such groups can include non-hydrocarbon functionalities such as ester, ether, halogen, ketone, sulfide, sulfone, nitrile and silane. For example, included within the scope of $R^2N=C=O$ are 2-isocyanatoethyl methacrylate; isocyanato methacrylate; and chlorosulfonyl isocyanate.

In Process A of the present invention, the reaction between the cyclosilazane and the isocyanate containing moiety takes place such that the product is a silylurea in which one of the urea nitrogen atoms is bonded to a silicon atom with both the nitrogen atom and the silicon atom being contained in the cyclosilazane ring. In Process A, reaction conditions are not narrowly critical due to the ease of reaction. In general, Process A occurs at a temperature ranging from about −10° C. to 100° C., preferably 0° C. to 70° C., and most preferably 0° C. to 50° C. Process A is conducted under a dry atmosphere of an inert gas such as nitrogen or argon, preferably nitrogen, under ambient pressure. While superatmospheric and subatmospheric pressures can be employed, generally, such pressures are not required or desired.

Optionally, an inert solvent can be employed to reduce viscosity of one or more of the reactants and/or to moderate the heat generated in Process A. Typically, such solvent can include aliphatic and aromatic hydrocarbons such as hexane, heptane, octane, toluene, xylene, and the like, and mixtures thereof. Petroleum ethers having a variety of boiling point ranges can be employed. Polar solvents such as tetrahydrofuran, acetonitrile, dimethyl formamide, and dimethylsulfoxide, can also be employed in Process A, if desired.

Additionally, a catalyst can be used in Process A, if desired. Catalysts useful to accelerate isocyanate addition reactions are readily available and well known to those skilled in the art. Most commonly employed catalysts are tertiary amines such as, for example, triethylamine and N-ethylmorpholine, and the like.

Process A can be performed using a wide variety of equipment that has provision for heating and cooling, maintenance of an inert atmosphere, agitation, and ancillary devices, if desired, for filtration, stripping of solvents, and transfer of products.

Cyclosilazane

Any cyclosilazane having the above Formula I can be used to make the cyclic silylurea of the present invention.

Illustrative cyclosilazanes which can be employed in the process for preparing a cyclic silylurea of the present invention include:

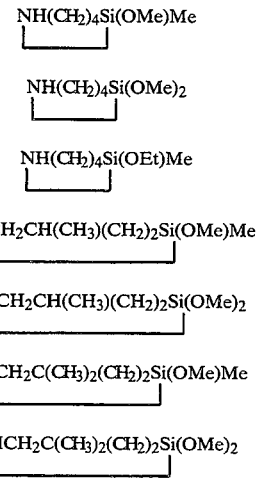

Cyclosilazanes of Formula I which can be used in Process A to make the cyclic silylurea (Formula III) can be prepared in accordance with Process B of the present invention as follows:

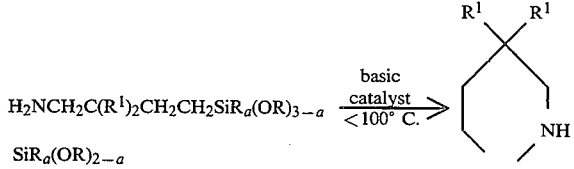

In Formula IV, R, $R^1$ and a are as defined hereinabove with respect to Formulae I and III. Preferably, in Formulae I and IV, each $R^1$ is a methyl or one $R^1$ is a methyl group and the other $R^1$ is a hydrogen. Most preferably, at least one $R^1$ is a linear or branched alkyl group having 1 to 6 carbon atoms or an aryl group having 6 to 8 carbon atoms.

The preferred aminoalkylalkoxysilanes that can be employed in Process B of the present invention include the following:

$H_2NCH_2CMe_2CH_2CH_2SiMe(OMe)_2$*
$H_2NCH_2CMe_2CH_2CH_2SiMe(OEt)_2$*
$H_2NCH_2CMe_2CH_2CH_2SiMe_2(OMe)$
$H_2NCH_2CHMeCH_2CH_2SiMe(OMe)_2$
$H_2NCH_2CHMeCH_2CH_2SiMe(OEt)_2$
$H_2NCH_2CHMeCH_2CH_2SiMe_2(OMe)$
$H_2NCH_2CH_2CH_2CH_2SiMe(OMe)_2$
$H_2NCH_2CH_2CH_2CH_2SiMe(OEt)_2$
$H_2NCH_2CH_2CH_2CH_2SiMe_2(OMe)$
$H_2NCH_2CMe_2CH_2CH_2SiMe(OPr)_2$*
$H_2NCH_2CH_2CH_2CH_2SiEt(OMe)_2$
$H_2NCH_2CMe_2CH_2CH_2Si(OMe)_3$
$H_2NCH_2CMe_2CH_2CH_2Si(OEt)_3$
$H_2NCH_2CMe_2CH_2CH_2SiMe_2(OEt)$
$H_2NCH_2CHMeCH_2CH_2Si(OMe)_3$
$H_2NCH_2CHMeCH_2CH_2Si(OEt)_3$
$H_2NCH_2CHMeCH_2CH_2SiMe_2(OEt)$
$H_2NCH_2CH_2CH_2CH_2Si(OMe)_3$
$H_2NCH_2CH_2CH_2CH_2Si(OEt)_3$
$H_2NCH_2CH_2CH_2CH_2SiMe_2(OEt)$
$H_2NCH_2CMe_2CH_2CH_2Si(OPr)(OMe)_2$

*Me is methyl Et is ethyl Pr is propyl

It has been found that when the $R^1$ group is a methyl group, the cyclization reaction is unexpectedly facilitated. Most of such aminoalkylalkoxysilanes can be prepared by methods well known to those skilled in the art. Such methods include, for example, the hydrogen reduction of the corresponding nitrile-substituted alkylalkoxysilanes as disclosed in U.S. Pat. No. 2,930,809. Process B of the present invention is so facile that it is not necessary to isolate the aminoalkylalkoxysilanes after such reduction. The novel cyclosilazanes of Process B of the present invention are distilled directly from the reduction reaction mixture after simple addition of the base catalyst.

The corresponding nitrile-substituted alkylalkoxysilanes or precursors are also well known in the art and are readily commercially available, except for the nitrile-substituted alkylalkoxysilanes which contain the $-CH_2CH_2CMe_2CN$ substituent. These latter nitrile-substituted alkylalkoxysilanes are obtained in accordance with Process C of the present invention described hereinbelow. The nitrile-substituted alkylalkoxysilanes which contain the $-CH_2CH_2CMe_2CN$ substituent have sterically hindered nitrile groups attached to the quaternary carbon atoms. Hydrogen reduction thereof results in the aminoalkylalkoxy-silanes in accordance with Process C.

Process B is conducted in the presence of a basic catalyst. The basic catalyst used in Process B is a nonvolatile base of sufficient strength to catalyze the reaction, but not such that it reacts with other substituents of the aminoalkylalkoxysilane (Formula IV). It is desirable that the basic catalyst be soluble in the reaction mixture and that it not promote undesired side reactions. Therefore, preferred basic catalyst are alkali metal salts of alcohols corresponding to the alkoxy group on the aminoalkylalkoxysilane (Formula IV). For example, methoxide salts are used with aminoalkylmethoxysilanes and ethoxide salts are employed with aminoalkylethyoxysilanes. Any alkali metal (sodium, potassium, lithium, and cesium) alkoxide can be employed as a basic catalyst in Process B of the present invention. However, sodium alkoxides such as sodium methoxide and sodium ethoxide are particularly preferred. The amount of basic catalyst employed in Process B is not narrowly critical and can range from about 0.01 to 10 weight percent, preferably from about 0.05 to 2 weight percent based on the amount of aminoalkylalkoxysilane employed.

Process B is conducted at a temperature less than 100° C. Preferably, the temperature ranges from about 40° C. to 90° C., most preferably it ranges from about 60° C. to 85° C. Process B of the present invention is carried out under a vacuum pressure ranging from about 0.1 to 20 millimeters of mercury, preferably 0.5 to 10 millimeters of mercury, and most preferably 1 to 7 millimeters of mercury. In Process B of the present invention lower levels of catalyst and milder reaction conditions (lower temperatures and less severe vacuum values) can be used as the number of $R^1$ groups which are methyl, rather than hydrogen, is increased.

The equipment used to perform Process B of the present invention is not narrowly critical. Process B can be performed in a variety of laboratory and commercial apparatus, ranging from standard or specialized glassware to stainless steel kettles, which have provisions for charging of reactants, heating and cooling, agitation, maintenance of appropriate vacuum or inert atmosphere, and removal of products, with ancillary equipment as needed for filtration, stripping of solvents, and distillation. Generally, Process B is conducted under an atmosphere of a dry inert gas such as nitrogen or argon.

Incorporation of Silylurea into Sealant Formulation

Cyclic silylureas of the present invention are used as highly moisture reactive precursors to silanol functionalities. That is, in the presence of water, the Si—N bond of the cyclic silylurea readily breaks to form a linear alkylurea. The silicon atom of the linear alkylurea readily accepts an OH—group, thereby becoming more easily susceptible to further crosslinking (—Si—O—Si—). Hence, when a cyclic silylurea is employed as a component in a sealant or caulking material, the sealant dries more quickly. For example a cyclic silylurea can be used as a reactive crosslinker for a neutral cure silicone rubber.

Any person skilled in moisture curable sealant formulating would know how to incorporate a cyclic silylurea into a sealant. See for example, *Caulks and Sealants, Volumes I and II*, Short Course Materials, The Adhesives and Sealants Council, Inc., Washington, D.C. (1992). In general, a dry filler is combined or mixed using agitation means with a mixture of a polymer or prepolymer, catalyst, and curing agent. Optionally, one or more of a solvent, plasticizer and extender are also used.

Process for Making an Aminoalkylalkoxysilane

Aminoalkylalkoxysilanes that can be used in the preparation of cyclosilazanes employed in Process B of the present invention can be made according to the following Process C:

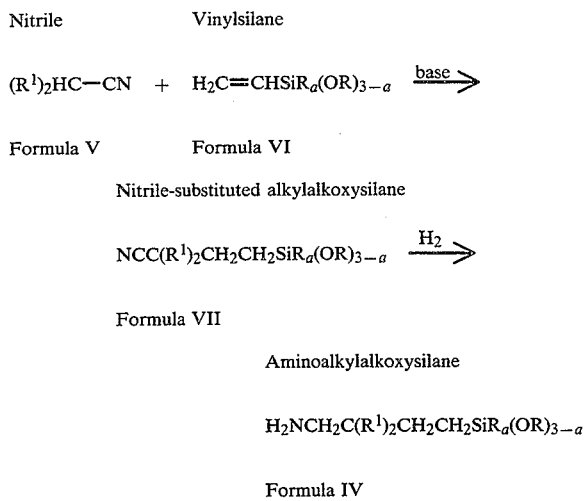

In Process C, above, it is understood that R, $R^1$ and a of Formulae IV through VII are as defined hereinabove with respect to Formulae I and III. Preferably, in the formulae of Process C, each R is a methyl group or an ethyl group; and each $R^1$ is a methyl group.

In Process C, a nitrile (Formula V) is reacted with a vinylsilane (Formula VI) with heating in the presence of a base at or near atmospheric pressure to produce a nitrile-substituted alkylalkoxysilane (Formula VII). Reaction temperatures may vary from about 50° C to 150° C., depending upon the base used to catalyze the reaction. Preferably, the reaction temperature ranges from about 110° C. to 130° C. Preferably, the reaction is carried out with agitation at atmospheric pressure. Optionally the reaction may be performed in the presence of an inert solvent such as xylene in an amount ranging from 10 to 200 percent based on the total weight of the reactants.

The base used to catalyze the reaction of the nitrile (Formula V) and vinylsilane (Formula VI) is selected from the group consisting of: (a) an alkali metal (sodium, potassium, cesium, and lithium); (b) an alkali metal alkoxide such as sodium or potassium methoxide; (c) an alkali metal amide such as sodium amide; (d) an alkali metal hydride such as sodium hydride; (e) and mixtures thereof. While any alkali metal, alkali metal-alkoxide, -amide, or -hydride can be used, preferably the metal is sodium. Most preferably, sodium metal is employed in order to minimize undesirable side reactions.

While the nitrile-substituted alkylalkoxysilane (Formula VII) is hydrogenated by any means known to one skilled in the art to produce the aminoalkylalkoxysilane (Formula IV), the reduction of nitrile-substituted alkylalkoxysilanes in which the nitrile-bearing carbon atom is attached to a quaternary carbon atom provides aminoalkylalkoxysilanes bearing neopentylamine groups (i.e., where $R^1$=Me or methyl groups(s)). Such silanes provide properties (i.e., reactivity, basicity, resistance to oxidative color development) intermediate between 3-aminopropylalkoxysilanes and the sterically hindered 3-amino-3,3-dimethylpropylalkoxysilanes as disclosed in U.S. Pat. Nos. 5,030,746 and 5,082,962. Such hydrogenation is disclosed, for example, in U.S. Pat. No. 2,930,809. In general, aminoalkylalkoxysilanes are prepared by reacting a nitrile-substituted alkylsilane in the presence of a Raney Ni catalyst or similar catalyst at an elevated temperature (120° C. to 200° C.) and super atmospheric pressure (100 to 2,000 psi).

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLE 1

Preparation of 1-Methyl-1-methoxysila-2-aza-4-methylcyclohexane

4-Amino-3-methylbutylmethyldimethoxysilane (162 grams, 0.84 moles) was charged to a 500-milliliter, three-necked flask equipped with magnetic stirring bar assembly, thermometer, electric heating mantle and attached to a (1 ft.×¾ in. diameter) Vigreaux column equipped for vacuum distillation. While stirring the mixture, sodium methoxide (0.8 grams, 0.015 moles) was added and the mixture was heated at 85° C. at 5.0 mm Hg pressure for 25 hours while slowly removing methanol vapor to a Dry Ice ™ trap and a distillate product having a boiling point of 60°±2° C. at 5 mm Hg pressure was removed to a receiver flask. The crude distillate product was redistilled through a column (2 ft.×1 in. diameter) packed with ⅛-inch, helix-shaped glass equipped for vacuum fractional distillation. The yield was 76 grams of 1-methyl-1-methoxysila-2-aza-4-methylcyclohexane having a boiling point of

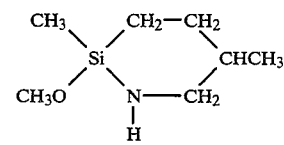

53° C. at 5.0 mm Hg pressure. Purity by gas chromatography analysis was 100%. The nitrogen assay was calculated to be 6.28 meq/gram [6.1 meq/gram actual]. The $^1$H NMR, $^{13}$C NMR, $^{29}$Si NMR and gas chromatography interfaced to a mass analyzer operating in the electron beam ionizing mode (EI) confirm the structure and purity of the conformational isomers of both the cyclic silazane above and the n-butyl isocyanate adduct derivative described in Example 10.

EXAMPLE 2

Preparation of 1,1-Dimethoxysila-2-aza-4-methylcyclohexane

4-Amino-3-methylbutyltrimethoxysilane (157 grams, 0.757 moles) was charged to a flask equipped as in Example 1. Sodium methoxide (3.1 grams, 2 wt %) was added and the stirred mixture was heated at 80°±5° C. over 6 hours at 2±1 mm Hg pressure while slowly removing methanol vapor to a Dry Ice ™ trap and distillate product having a boiling point of 57°±5° C. was removed to a receiver flask. The crude distillate product was redistilled through a column (2 ft.×1 in. diameter) packed with helix-shaped, ⅛ inch glass equipped for vacuum fractional distillation. The yield was 102.7 grams (0.586 moles) of 1,1-dimethoxysila-2-aza-4-methylcyclohexane,

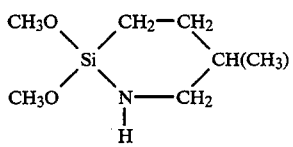

having a boiling point of 73°±1° C. at 3.8°±0.2 mm Hg pressure. Purity by gas chromatography was 98%. The nitrogen assay was calculated to be 5.7 meq./gram [5.68 meq/gram actual].

EXAMPLE 3

Preparation of
1,1-Dimethoxysila-2-aza-4,4-dimethycyclohexane

4-Amino-3,3-dimethylbutyltrimethoxysilane (208.3 grams, 1.014 moles) was charged to a flask equipped as in Example 1. Sodium methoxide (2 grams, 1.0 weight %) was added as described in Example 2. According to analysis using gas chromatography, the crude distillate product (176.9 grams) had 49% cyclic silazane. The crude product was redistilled as in Example 2. The yield was 90 grams (0.47 moles) of 1,1-dimethoxysila-2-aza-4,4-dimethylcyclohexane,

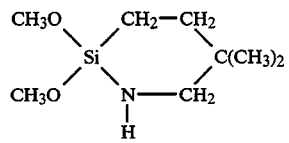

having a boiling point of 39°±1° C. at 0.30 mm Hg pressure. Purity by gas chromatography was 100%. The nitrogen assay was calculated to be 5.28 meq/gram [5.30 meq/gram actual].

EXAMPLE 4

Preparation of
1-Methoxy-1-methylsila-2-aza-4,4-dimethycyclohexane

4-Amino-3,3-dimethylbutylmethyldimethoxysilane (134.9 grams, 0.65 moles) was charged to a flask equipped as in Example 1. Sodium methoxide (1.3 grams, 1.0 weight %) was added, and the mixture was heated at 99° C. to 103° C. at 1.3 mm Hg pressure over 4 hours while slowly removing methanol vapor to a Dry Ice TM trap. Distillate (106.3 grams) boiling at 49° C. to 67° C. consisted of 31.2% cyclic silazane with 68.6% starting aminoorganosilane. Redistillation as described in Example 2 of combined distillate from several runs produced 51 grams (0.29 moles) of 1-methoxy-1-methysila-2-aza-4,4-dimethylcyclohexane,

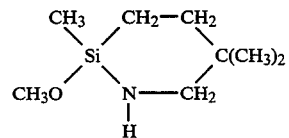

having a boiling point of 35°±1° C. at 0.30 mm Hg pressure. Purity by gas chromatography was 100%. The nitrogen assay was calculated to be 5.77 meq/gram [5.80 meq/gram actual].

EXAMPLE 5

Preparation of
1-Methyl-1-methoxysila-2-azacyclohexane

4-Aminobutylmethyldimethoxysilane (100 grams, 0.56 moles) was charged to a flask equipped as described in Example 1. Sodium methoxide (1 gram, 1.0 weight %) was added and the mixture heated at 120°±2° C. at 41 mm Hg pressure while slowly removing methanol vapor to a Dry Ice TM trap. Distillate (9.3 grams) boiling at 88° C. to 102° C. was removed to a receiver flask. Gas chromatographic analysis showed a mixture of 13% cyclic silazane product and 87% starting aminoorganosilane. Heating the reaction mixture for an additional six hours at 90°±2° C. at 6±1 mm Hg pressure produced 28.3 grams of distillate boiling at 70° C. to 80° C. Analysis of the distillate showed 60% cyclosilazane with 40% starting aminoorganosilane. Redistillation as described in Example 2 produced 50 grams (0.34 moles) of 1-methyl-1-methoxysilyl-2-azacyclohexane,

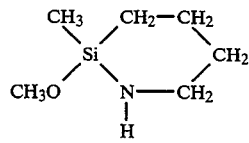

having a boiling point of 70°±1° C. at 7.0 mm Hg pressure. Purity by gas chromatographic analysis was 99%. The nitrogen assay was calculated to be 6.88 meq/gram [6.80 meq/gram actual].

EXAMPLE 6

Preparation of
3-Cyano-3-methylbutylmethyldimethoxysilane

To a 2-liter, four-necked glass flask equipped with a heating mantle, mechanical stirrer, thermometer, dropping funnel and water condenser, isobutyronitrile (345.0 grams, 5.0 moles) and sodium metal spheres (11.5 grams, 0.5 moles) were added under a nitrogen atmosphere. The temperature of the flask contents exothermically rose to 45° C. and the contents in the flask were heated to 100° C. Using an addition funnel, methylvinyldimethoxysilane (661.3 grams, 5.0 moles) was added to the contents in the flask. During the reaction, the heating mantle was removed, and the temperature of the contents in the flask was maintained at 105° to 115° C. by the rate of addition of the methylvinyldimethoxysilane. Upon completion of methylvinyldimethoxysilane addition, the contents of the flask were heated to 150° C. for one hour, and then cooled to room temperature. Glacial acetic acid (36 grams, 0.6 moles) was added to neutralize residual basic material. The product was filtered and distilled (boiling point 86° C. to 88° C. at 3.0 mm Hg) to yield 726 grams (72% yield after distillation) of 3-cyano-3-methylbutylmethyldimethoxysilane, as characterized by $^1$H and $^{13}$C NMR spectroscopy.

EXAMPLE 7

Preparation of
4-Amino-3,3-dimethylbutylmethyldimethoxysilane

To a 1-liter, high-pressure, stirred autoclave was added a mixture of 3-cyano-3-methylbutylmethyldimethoxysilane (631 grams, 3.13 moles) containing 12.0 grams of dissolved ammonia and 8.5 grams of nickel (5%) on kieselguhr. The autoclave was sealed, pressurized to 800 psi with hydrogen and heated for 10 hours. The contents were cooled and the product was collected, filtered, and distilled. The yield was 615.9 grams (95.9% yield after distillation) of 4-amino-3,3-dimethyl-butylmethyldimethoxysilane, as characterized by $^1$H and $^{13}$C NMR spectroscopy.

EXAMPLE 8

Preparation of 3-Cyano-3-methylbutyltrimethoxysilane

Under a nitrogen atmosphere, isobutyronitrile (297.4 grams, 4.3 moles) and sodium metal spheres (9.9 grams, 0.43 moles) were added to a flask as described in Example 6. The contents of the flask were heated to 103° C with stirring and vinyltrimethoxysilane (637.8 grams, 4.3 moles) was added. After removing the heat source, the temperature of the flask contents was maintained at 100° C. to 107° C. by the rate of addition of the vinyltrimethoxysilane. After adding all of the vinyltrimethoxysilane, the flask contents were heated to 150° C. for one hour to ensure complete reaction. A sample taken for infra-red analysis showed no signs of any absorption attributable to a vinyl group on silicon. The infra-red spectrum was entirely consistent with the proposed structure and indicated a high state of purity. After cooling to room temperature, 25.8 grams (0.43 moles) of glacial acetic acid was added to neutralize any residual basic material. The reaction product was filtered and vacuum distilled (boiling point, 76° C. to 77° C. at 0.3 mm Hg) to yield 681.4 grams (73% yield after distillation) of 3-cyano-3-methylbutyltrimethoxysilane, as characterized by $^1$H and $^{13}$C NMR spectroscopy.

EXAMPLE 9

Preparation of 4-Amino-3,3-dimethylbutyltrimethoxysilane

In accordance with the procedure in Example 7, 3-cyano-3-methylbutyltrimethoxysilane (600 grams, 2.76 moles) was hydrogenated in the presence of 10.0 grams of ammonia and 8.0 grams of nickel (5%) on kieselguhr. The yield after distillation (boiling point, 68° C. at 0.25 mm Hg) was 590 grams of 4-amino-3,3-dimethylbutyltrimethoxysilane (96.6%). The material was characterized by infra-red, $^1$H and $^{13}$C NMR spectroscopy.

COMPARATIVE EXAMPLE I

Unsuccessful Preparation of 1,1-Dimethoxysila-2-azacyclopentane

The procedure of Example 1 was repeated, except that 3-aminopropyltrimethoxysilane (113.5 grams; 0.63 moles) was used. Sodium methoxide (2.3 grams, 2 wt.%) was added. The reaction mixture was stirred and heated to 90° C. to 98° C. for 6 hours at 4-8 mm Hg, while slowly removing distillate. However gas chromatographic analysis indicated 1,1-dimethoxysila-2-azacyclopentane was not formed. The distillate consisted of >99% 3-aminopropyltrimethoxysilane. The reaction mixture was further heated to 130° C. (>10 mm Hg) but distillate analysis again indicated no five-membered ring cyclosilazane product was formed.

EXAMPLE 10

Reaction of 1-Methyl-1-methoxysila-2-aza-4-methylcyclohexane with n-butyl isocyanate 1-Methyl-1-methoxysila-2-aza-4-methylcyclohexane (15.9 grams, 0.1 moles) and hexane (25 gms.) were charged to a 250 milliliter three-necked flask equipped with magnetic stirring bar assembly, thermometer and dropping funnel. The flask was immersed in an ice bath and the mixture was cooled to about 3° C. under an atmosphere of dry nitrogen gas. n-Butyl isocyanate (10.9 grams, 0.11 moles) was added dropwise for five minutes from a dropping funnel. The reaction mixture was heated under vacuum to 40° C. at 1 mm Hg pressure to remove hexane and excess n-butyl isocyanate. A white solid residue product (26.5 grams) melting at 65° C. having the structure:

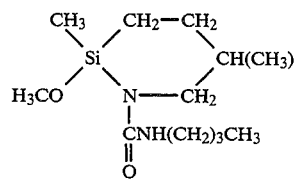

was produced.

EXAMPLE 11

Reaction of 1-Methyl-1-methoxysila-2-aza-4-methycyclohexane with isocyanate-terminated polyurethane prepolymer Isocyanate-terminated Polyurethane Prepolymer Tetraethylene glycol (349.6 grams, 1.8 moles) and 613 grams of 2-butanone were charged to a two-liter, three-necked flask equipped with mechanical stirrer, thermometer, water condenser, electric heating mantle and dropping funnel. The mixture was subjected to vacuum stripping at 30° C. and 30 grams of 2-butanone and trace amounts of water were removed to a Dry-Ice ™ trap. Under a dry nitrogen atmosphere, stannous octoate (0.175 grams, 0.02% by weight) was added. The mixture was heated to gentle reflux at approximately 80° C. and bis-(4-isocyanatocyclohexyl) methane (514.7 grams, 2.0 moles) was added over one hour. After six hours at 80° C., the reaction mixture was cooled to room temperature to produce a 60 wt % solution of isocyanate-terminated polyurethane prepolymer. A small sample was removed and titrated to determine the amount of isocyanate using a standard solution of dibutyl amine in 2-butanone. The concentration of isocyanate was 0.23 moles/kilogram. The neat concentration of isocyanate was 0.38 moles/kilogram, which corresponded to a molecular weight of approximately 5260 gms/mole.

Control A

Isocyanate-terminated polyurethane prepolymer (300 grams, 0.069 moles NCO) solution was charged to a 500 milliliter, three-necked flask equipped with a mechanical stirrer, electric heating mantle, thermometer and dropping funnel. Under an atmosphere of dry nitrogen, 4-amino-3-methylbutylmethyldimethoxysilane (13.2 grams, 0.069 moles) was added to the flask with stirring at 50° C. for five minutes. After stirring for an additional 30 minutes at 70° C., a polyurethane prepolymer having linear silane endcapping was diluted with dry 2-butanone to 50 wt % solids and stored in a sealed bottle.

Novel Cyclosilazane

The procedure of Control A was repeated except that 1-methyl-1-methoxysila-2-aza-4-methylcyclohexane (10.98 grams, 0.069 moles) was used instead 4-amino-3-methylbutylmethyldimethoxysilane to produce a polyurethane prepolymer having a cyclosilazane endcapping.

EXAMPLE 12

RTV Cure Rates for Control A and Novel Cyclosilazane-Capped Polyurethane Prepolymer A bead of Control A was applied to each of the following panels: polyethylene, Mylar TM, Teflon TM, steel, aluminum, glass plate, and painted glass. A bead of cyclosilazane endcapped polyurethane prepolymer was similarly applied to another set of the panels. The time required in air to develop a "tack-free" bead was observed. The panels treated with the novel cyclosilazane end-capped polyurethane prepolymer of the present invention became tack-free in a much shorter amount of time than those of Control A. Two more sets of panels treated with beads of Control A and the novel cyclosilazane end-capped polyurethane prepolymer were prepared as above and placed in an oven at 70° C. for 3 hours. It was observed that the beads on the panels treated with the cyclosilazane end-capped polyurethane prepolymer were firmer than those of Control A. These tests were repeated using some of the same materials prepared in Example 11 after the prepolymers had been stored in sealed bottles for six months. Again it was observed that the beads on panels treated with the cyclosilazane end-capped polyurethane prepolymer cured faster than those of Control A.

EXAMPLE 13

Cure Rates of Sealants Containing Linear Silanes and Cyclosilazanes

Prepolymer Preparation

To a dry 500-milliliter resin flask, equipped with a mechanical stirrer, heating mantle, thermometer, and condenser was added 4,4'-diphenylmethane diisocyanate (23 gm., 0.092 moles) purchased from Miles, Inc. and polypropylene glycol, (245.8 gm., about 4000 mol. wt., OH Number=28.0) commercially available as PPG-D-4000 from Olin Chemicals Inc. The molar ratio of 4,4'-diphenylmethane diisocyanate to polypropylene glycol was 1.5. The contents of the flask were heated to 50° C. until the reaction mixture became liquid, then one drop of dibutyltin dilaurate catalyst was added to the reactants. The mixture was heated to 80°–90° C. until the concentration of isocyanate groups decreased to about 0.8%. After cooling to room temperature, the contents of the flask (an isocyanate functional polyether prepolymer) were used as described below.

Control B

To 80 grams of the prepolymer was slowly added 3.46 grams (10 mole % excess, based on NCO content) of 4-amino-3-methylbutyltrimethoxysilane at room temperature in equipment as set forth in Example 11. After the addition was complete, the composition was heated with stirring to 90° C. until the isocyanate concentration was 0% by titration.

Control C

In a manner similar to that of Control B, a second 80 gram portion of the prepolymer was reacted with 3.00 grams (10 mole % excess, based on NCO content) of 3-aminopropyltrimethoxysilane.

Novel Cyclosilazane (Run No. 1)

In a manner similar to the preparation of Controls B and C, a third 80 gram portion of prepolymer was reacted with 2.93 grams (10 mole % excess, based on NCO content) of 1,1-dimethoxysila-2-aza-4methylcyclohexane.

Sealant Preparation

Sealants were prepared from each of these three silylurea linked polymers by using a small planetary mixer equipped with a vacuum pump, a temperature bath, and nitrogen and air lines. The mixer was heated to 80° C. with nitrogen purging through the system for 30 minutes. Each silylurea linked polymer (80 gm.) was placed in the heated mixer, along with 24 grams of calcium carbonate filler (available as Ultra-Flex TM from Pfizer Corporation). The materials were mixed for five minutes under a nitrogen atmosphere at a speed of 40 rpm. Each of the sealant compositions was mixed under vacuum for 50 minutes. The temperature was reduced to 60° C. and 0.8 grams of dibutyltin dilaurate was added to each mixture. Each composition was mixed for 5 minutes in a nitrogen atmosphere followed by vacuum treatment for an additional 50 minutes. Each sealant was removed from the mixer and stored in an aluminum foil/cardboard cartridge.

Tack free times for each sealant were determined. Each sealant was charged to a 4"×8"×⅛" Teflon mold. Each mold was placed in a humidity chamber at 23° C. and 50% relative humidity. The time required for each of the surfaces to become tack free to the touch was recorded. The results were:

| | | |
|---|---|---|
| Control B: | 4-amino-3-methylbutyltrimethoxysilane capped polymer | 0.5 hour |
| Control C: | 3-aminopropyltrimethoxysilane capped polymer | 2.0 hours |
| Run No. 1: | 1,1-dimethoxysila-2-aza-4-methylcyclohexane capped polymer | 0.01 hour |

This example illustrates that sealants derived from the novel cyclosilazane-capped polyurethane prepolymers of the present invention cure much more rapidly than those prepared from polyurethane prepolymers capped with linear aminoalkylalkoxysilanes.

What is claimed is:

1. A cyclic silylurea having the formula:

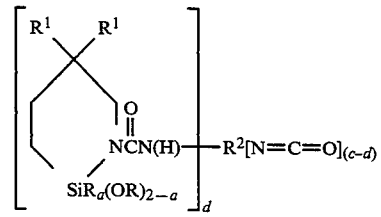

wherein
R is an alkyl group having 1 to 3 carbon atoms;

$R^1$ is selected from the group consisting of
(i) hydrogen,
(ii) a linear or branched alkyl group having 1 to 6 carbon atoms, and
(iii) an aryl group having 6 to 8 carbon atoms;
$R^2$ is a mono, di, or polyvalent organic or organosilicone monomer or polymer;
a is 0, 1, or 2;
c is a number ranging from 1 to 5 inclusive; and
d is a number less than or equal to c.

2. The cyclic silylurea of claim 1 wherein R is a methyl group or an ethyl group; $R^1$ is a hydrogen or a methyl group; and $R^2$ is selected from the group consisting of
(i) a alkyl hydrocarbon group having 1 to 11 carbon atoms;
(ii) a aryl group having 6 to 16 carbon atoms;
(iii) an arylene group having 7 to 20 carbon atoms;
(iv) an alkarylene having 7 to 28 carbon atoms;
(v) an alkylene group having 2 to 18 carbon atoms; and
(vi) a polymeric moiety.

3. The cyclic silylurea of claim 1 wherein $R^2$ is polymeric moiety selected from the group consisting of
(i) a polyester,
(ii) a polyether,
(iii) a polydiene,
(iv) a polyurethane,
(v) a poly(meth)acrylate, and
(vi) a polyorganosilicone.

4. The cyclic silylurea of claim 1 wherein each R is a methyl group; one $R^1$ is a hydrogen and the other $R^1$ is a methyl group; each of a, c and d is 1 and $R^2$ is a n-butyl group.

5. The cyclic silylurea of claim 1 wherein R is a methyl group; one $R^1$ is a hydrogen and the other $R^1$ is a methyl group; a is 1; each of c and d is 2; and $R^2$ is a polyurethane prepared from tetraethylene glycol and an excess of bis-(4-isocyanatocyclohexyl)methane.

6. A process for making a cyclic silylurea of claim 1 which process comprises contacting a cyclosilazane having the formula:

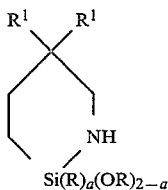

$Si(R)_a(OR)_{2-a}$ wherein
R is an alkyl group having 1 to 3 carbon atoms;
$R^1$ is selected from the group consisting of
(i) hydrogen,
(ii) a linear or branched alkyl group having 1 to 6 carbon atoms,
(iii) an aryl group having 6 to 8 carbon atoms; and
a is 0, 1, or 2;
with an isocyanate containing moiety having the formula:

wherein
$R^2$ is a mono, di, or polyvalent organic or organosilicone monomer or polymer; and c is a number ranging from 1 to 5 inclusive.

7. The process of claim 6 wherein R is selected from the group consisting of a methyl group and an ethyl group; $R^1$ is selected from the group consisting of a hydrogen and a methyl group; and
$R^2$ is selected from the group consisting of
(i) an alkyl group having 1 to 11 carbon atoms,
(ii) an aryl group having 6 to 16 carbon atoms,
(iii) an arylene group having 7 to 20 carbon atoms,
(iv) an alkarylene having 7 to 28 carbon atoms, and
(v) an alkylene group having 2 to 18 carbon atoms; and
(vi) a polymeric moiety.

8. The process of claim 6 wherein R is a methyl group; one $R^1$ is a hydrogen and the other $R^1$ is a methyl group; each of a, c and d is 1; and $R^2$ is a n-butyl group.

9. The process of claim 6 wherein each R is a methyl group; one $R^1$ is a hydrogen and the other $R^1$ is a methyl group; a is 1; each of c and d is 2; and $R^2$ is a polyurethane prepared from tetraethylene glycol and an excess of bis-(4-isocyanatocyclohexyl)methane.

10. A sealant formulation containing the cyclic silylurea of claim 1, and a filler and a catalyst.

11. A cyclosilazane having the formula:

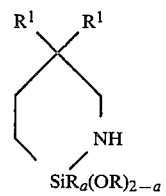

$SiR_a(OR)_{2-a}$ wherein
R is an alkyl group having 1 to 3 carbon atoms;
$R^1$ is selected from the group consisting of
(i) hydrogen
(ii) a linear or branched alkyl group having 1 to 6 carbon atoms, and
(iii) an aryl group having 6 to 8 carbon atoms; and
a is 0, 1, or 2.

12. The cyclosilazane of claim 11 wherein R is a methyl group and at least one $R^1$ is a methyl group.

13. A process for making a cyclosilazane having the formula:

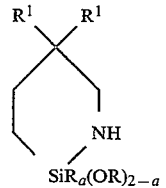

$SiR_a(OR)_{2-a}$ wherein
R is an alkyl group having 1 to 3 carbon atoms;
$R^1$ is selected from the group consisting of
(i) hydrogen;
(ii) a linear or branched alkyl group having 1 to 6 carbon atoms;
(iii) an aryl group having 6 to 8 carbon atoms; and
a is is 0, 1, or 2; and
which process comprises heating an aminoalkylalkoxysilane having the formula:

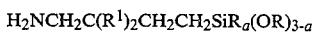

wherein R, $R^1$, and a are as defined above in the presence of a basic catalyst at subatmospheric pressure and at a temperature less than 100° C.

14. The process of claim 13 wherein the basic catalyst is selected from the group consisting of a sodium alkoxide, a lithium alkoxide, potassium alkoxide and cesium alkoxide.

15. The process of claim 13 wherein R is a methyl group and at least one $R^1$ is a methyl group.

16. A process for making an aminoalkylalkoxysilane having the formula:

$$H_2NCH_2C(R^1)_2CH_2CH_2SiR_a(OR)_{3-a}$$

wherein
R is an alkyl group having 1 to 3 carbon atoms;
$R^1$ is selected from the group consisting of
(i) hydrogen;
(ii) a linear or branched alkyl group having 1 to 6 carbon atoms;
(iii) an aryl group having 6 to 8 carbon atoms; and
a is 0, 1, or 2; and
which process comprises:
(1) reacting a nitrile having the formula:

$$(R^1)_2HC\text{-}CN$$

wherein $R^1$ is as defined above with a vinyl silane having the formula:

$$H_2C=CHSiR_a(OR)_{3-a},$$ wherein a and R are as defined above while heating in the presence of a base selected from the group consisting of
(i) an alkali metal,
(ii) an alkali metal alkoxide,
(iii) an alkali metal amide; and
(iv) an alkali metal hydride;
to form a nitrile-substituted alkylalkoxysilane reaction product having the formula:

$$NCC(R^1)_2CH_2CH_2SiR_a(OR)_{3-a}; \text{ and}$$

(2) hydrogenating said reaction product.

17. The process of claim 16 wherein in the nitrile-substituted alkylalkoxysilane, R is methyl, $R^1$ is methyl, and a is zero or 1.

18. An aminoalkylalkoxysilane having the formula $$H_2NCH_2C(CH_3)_2CH_2CH_2SiR_a(OR)_{3-a}$$

wherein
R is an alkyl group having 1 to 3 carbon atoms and a is 0, 1, or 2.

19. A nitrile-substituted alkylalkoxysilane having the formula:

$$NCC(R^1)_2CH_2CH_2SiR_a(OR)_{3-a}$$

wherein R is an alkyl group having 1 to 3 carbon atoms, and $R^1$ is a methyl group and a is 0, 1 or 2.

* * * * *